United States Patent [19]

Kulli

[11] Patent Number: 4,904,242
[45] Date of Patent: Feb. 27, 1990

[54] PHLEBOTOMY SET WITH SAFETY RETRACTING NEEDLE

[76] Inventor: John C. Kulli, 30 Widewaters La., Pittsford, N.Y. 14534

[21] Appl. No.: 200,638

[22] Filed: May 31, 1988

Related U.S. Application Data

[63] Continuation-in-part of Ser. No. 43,691, Apr. 29, 1987, Pat. No. 4,747,381.

[51] Int. Cl.$^4$ ............................................... A61M 5/32
[52] U.S. Cl. ..................................... 604/110; 604/195; 188/763
[58] Field of Search ............... 604/110, 195, 197, 196, 604/198, 263, 413, 414; 128/763, 765

[56] References Cited

U.S. PATENT DOCUMENTS

| | | | |
|---|---|---|---|
| 4,592,744 | 6/1986 | Jagger et al. | 128/763 |
| 4,692,156 | 9/1987 | Haller | 128/763 |
| 4,747,829 | 5/1988 | Jacob et al. | 604/110 |
| 4,790,827 | 12/1988 | Habber et al. | 128/763 |

Primary Examiner—Stephen C. Pellegrino
Attorney, Agent, or Firm—Peter I. Lippman

[57] ABSTRACT

A hollow needle projects from the forward end of a needle is released from the handle and retracted. The ferrule, which is circumferentially grooved. The holder includes a handle to be grasped by a user, a frontal leaved structure for gripping the needle ferrule at its groove, and a rearward skirt for guarding the rear end of the needle. The rear of the needle is accessible within the skirt for attachment to vacuum vials, or to tubing for conducting liquid from the patient to a remote storage vessel. After use to withdraw liquid from a patient, the needle is raised from the handle and retracted. The release and retraction are manually actuated by a simple unitary rectilinear motion. Preferably the mechanism for initiating release and retraction includes a separate safety container that is inserted into the rear skirt of the holder in the same manner as a vacuum vial, but that receives and encloses the entire needle for disposal. This separate safety container carries at its forward end a fitting for manipulating the frontal structure of the holder to spread the leaves, extracting them from the groove in the ferrule and thereby releasing the needle; and also a rearward-spring-biased retractor for engaging the needle and drawing it into the safety container.

27 Claims, 3 Drawing Sheets

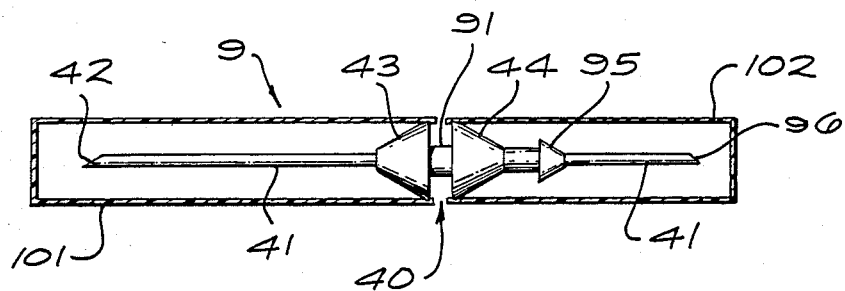
FIG. 1
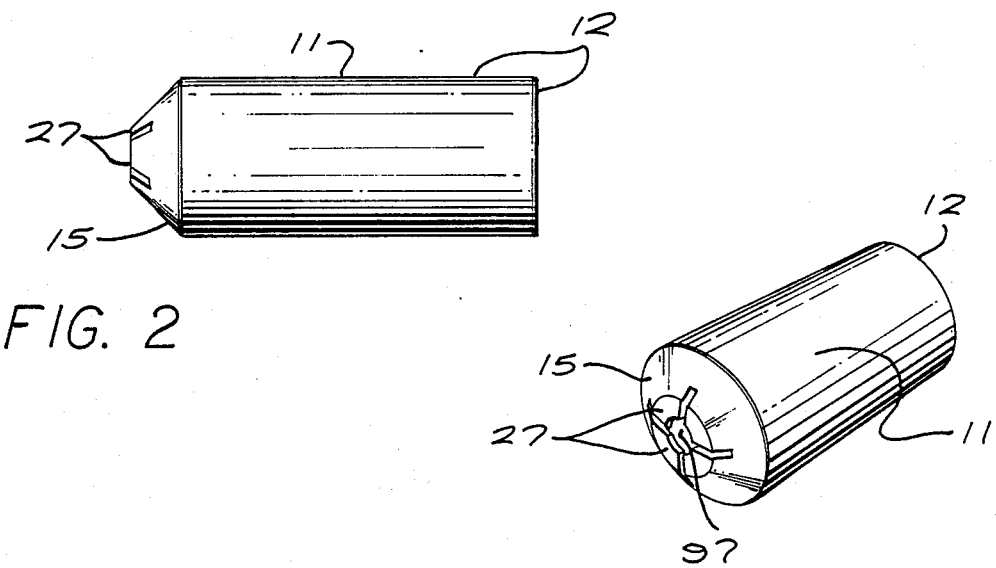
FIG. 2
FIG. 3
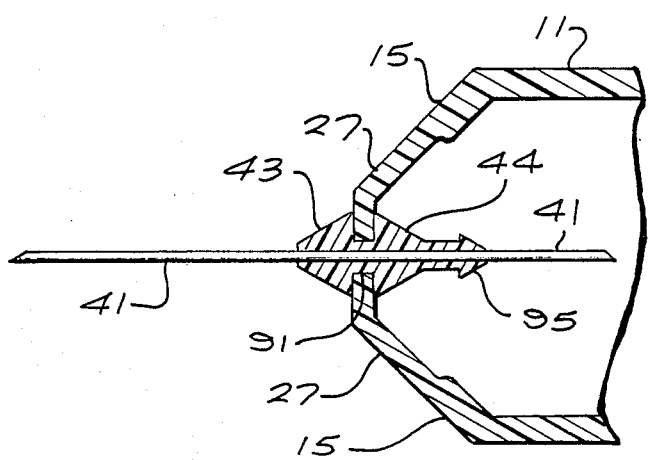
FIG. 4

PHLEBOTOMY SET WITH SAFETY RETRACTING NEEDLE

RELATED APPLICATION

This is a continuation-in-part of my copending U.S. Pat. Application 7/043,691, filed Apr. 29, 1987, and issuing on May 31, 1988, as U.S. Pat. No. 4,747,381.

BACKGROUND

1. Field of the Invention

This invention relates generally to medical appliances; and more particularly to a phlebotomy set for withdrawing liquids — usually blood — from a patient's body.

2. Prior Art

As is well known, there are myriad very important medical uses for withdrawing blood and other liquids from patients. It is also known that a severe problem has developed in relation to all such devices.

That problem arises from the continuing presence of horrible diseases, particularly fatal and currently incurable diseases such as acquired immune deficiency syndrome ("AIDS") and hepatitis, that are transmitted by exchange of body substances between people. These diseases have led medical institutions to exclusively use disposable needles for both injection and withdrawal of liquids from patients.

A severe residual risk remains, however, for medical personnel themselves in the inadvertent touching of needle tips after withdrawal from infected patients. Medical needles are designed and manufactured specifically to be extremely sharp and to puncture skin and flesh with only the slightest pressure.

As a result, what would ordinarily be an inconsequential scratch or pinprick can bring and has brought severe disease or even death to many medical staff members and others. Needless to say, health-care professionals are well aware of this risk and take considerable precautions to avoid such inadvertent punctures; thus the risk is reduced on a "probability" basis to an exceedingly small value.

Nevertheless, the exposure is so massive for working doctors, nurses and technicians that occasional punctures are inevitable. As a practical matter, it is virtually impossible for such an individual to reduce the incidence of accidental puncture to less than, say, one every year or perhaps one every few years.

Of course, not every such puncture follows contamination of the needle by a patient carrying a transmissible fatal disease. Nevertheless, there are enough medical personnel and enough such patients that a significant number of medical staffers die — and of course a greater number become very sick — from these accidents.

In discussion of this problem, needles of the types used with syringes commonly come to prominence. Though the word "hypodermic" has somewhat passed out of current usage in the medical profession, I shall for purposes of definiteness and simplicity refer to needles used with syringes for giving injections as "hypodermic needles." Needles used in drawing blood will be called "phlebotomy needles." By this terminology I mean to clearly distinguish all such needles from needles that are used for cannula insertion, the specific subject matter of my previously mentioned issued patent.

As detailed in that patent, the actual manual manipulations involved in using hypodermic and phlebotomy needles — as compared with cannula-insertion needles — are relatively favorable to avoiding puncture accidents. For that reason my first concern was for improvement of cannula-insertion needles.

The dangers of infection with hypodermic and phlebotomy needles nevertheless remain very important, partly because they are used in such enormous quantity. As noted in my patent, I did not mean to imply that hypodermic and phlebotomy needles are safe. There is an important potential for inadvertent unsheathing and many other kinds of accidents.

For example, as mentioned in my patent there are learning situations and emergencies, and circumstances in which the usual manual manipulations are complicated by patient mental or physical condition. While these situations are only a fraction of all instances of use of hypodermic and phlebotomy needles, this fraction nonetheless represents an enormous number of individual occurrences.

In a present-day standard, commercially available phlebotomy device — sometimes termed a "phlebotomy set" — the needle is stainless steel, hollow, and extremely sharp at its frontal end. The needle shank is threaded by the user onto a hollow handle, and more particularly to a transverse front end wall of the handle. The sharp end of the needle projects forward from the handle, and the rear end of the needle projects rearward into the interior of the handle.

The handle is generally a molded plastic cylinder, typically made of polycarbonate, open at the rear. The open rear portion of the handle forms a skirt that guards against casual contact with the rear end of the needle.

After assembly of the needle and handle, blood is collected in a separate liquid-receiving device, which usually takes one of two conventional forms. One such liquid-receiving unit is a remote receptacle, operated at a reduced internal pressure.

This remote receptacle communicates with the collection needle through a liquid-conveying long flexible tube, which is inserted through the open rear skirt of the handle and attached to the rear end of the needle. In a phlebotomy set designed for use with this type of receptacle, the rear end of the needle is cut off at right angles and given a smooth finish — to facilitate pushing the collection tube into place over the rear end of the needle.

With a remote receptacle, the sequence of procedural steps is somewhat variable. In principle the receptacle may be depressurized and the tubing connection completed before or after the system is connected to the patient's body.

In any case the sharp forward end of the needle is inserted into the patient's blood vessel — or in some cases possibly into a body cavity, or an abscess, or wherever fluid communication is to be established. The liquid to be collected flows through the needle and tubing into the remote receptacle, impelled by the difference between the blood pressure or other liquid pressure within the patient's body and the low pressure in the receptacle.

Another type of liquid-receiving unit known in present medical use is a vial that is sealed at a forward end by a piercable elastomeric wall or stopper. The vial is supplied at a reduced internal pressure.

In a phlebotomy set designed for use with this type of receptacle, the rearward end of the needle as well as the forward end is sharpened. In use, the sharp forward end of the collection needle is first inserted into position in the patient's body, and then the piercable wall of the collection vial is impaled on the sharp rear end of the collection needle. The liquid being collected flows into the evacuated vial under the influence of the pressure differential beween the liquid pressure within the patient's body and the pressure in the vial.

Phlebotomy devices for use with evacuated vials present a unique additional hazard — namely, the possibility of puncture at the sharp rear end of the needle. Since this end too carries the patient's possibly contaminated blood or other body fluid, all of the same dangers of infection mentioned earlier are operative here.

Typically a separate safety cover is supplied in place on at least the forward sharp end of the needle. The separate safety cover firmly grips the transverse wall of the handle, or a hub structure on the needle itself, and entirely covers the segment of the needle on one side of the tranverse wall.

This guarding prevents accidental puncture and accidental contamination of the needle by substances in the environment, before use. To use the needle, the safety cover must be entirely removed and set aside.

As already suggested, our focus of concern now shifts to the possibility that the needle may be contaminated by substances in the patient, during use. Accordingly the safety cover is to be replaced over the sharp end of the needle to prevent accidental puncture and particularly to prevent contact of people, other than the patient, with possible contaminants on the needle.

It is here that the prior art fails to be effective, since the process of replacing the safety cover — and in vacuum-vial devices two safety covers — is subject to many risks of inadvertent mishandling as previously mentioned.

The medical marketplace has seen various appliances and apparatuses aimed at solving these problems. One such device is a special form of hypodermic needle, available commercially from the firm ICU Medical, Inc. under the trade name "ICU High Risk Needle." The ICU device is fitted with a sliding sheath that is carried on the shaft of the hypodermic needle itself. After use the sheath is advanced forward over the needle tip.

That device undoubtedly serves a useful purpose, and could be adapted for use on phlebotomy-set needles. It is certainly not my desire to criticize what is apparently the only commercial effort directed to an important problem.

On the other hand, that device evidently has limitations that should be mentioned. First, the ICU High Risk Needle is offered as a special item at a special price, for use only with patients known to be "high risk" patients. Not all patients carrying transmissible fatal diseases are known to be high risks.

Secondly, the sheath is attached halfway out the needle, where there would appear to be potential for inadvertent application of lateral force with sufficient leverage to snap off the needle. If that should occur before the sheath were fully advanced, the potential for accidental puncture could be substantial.

Thirdly, it is not clear that the sheath when advanced locks in place firmly enough to withstand normal jarring in the workplace. It thus offers very limited protection.

Fourthly, an evacuated-vial phlebotomy set would require more than one sheath. That is, one would be required for each of the two sharp ends — doubling both the cost of manufacture and the attention required by medical personnel to secure the device after use.

Furthermore, reaching into the rear skirt to advance the sheath could itself be a hazardous procedure.

Fifthly and finally, the ICU needle is necessarily more than twice as long as a standard needle.

A number of patents have been issued for devices that shield medical needles. Among these is U.S. Pat. No. 4,592,744, issued June 3, 1986, to Janine C. Jagger et al. This patent illustrates and describes a device that facilitates retraction of a phlebotomy needle into a personnel-protective enclosure — which also serves as a handle for the device. The Jagger patent also shows and describes another device that similarly facilitates retraction of a hypodermic needle. In both of these devices the retraction procedure is relatively cumbersome.

In the Jagger phlebotomy device, which is of the evacuated-vial type, the final vial is used as a tool to unscrew the needle from a transverse wall at the forward end of the handle. This is done while the needle still pierces — and may damage — the elastomeric stopper.

To permit this unthreading, the vial carries a special dual boss at its forward end, adjacent to the piercable the stopper. When properly positioned by a user, the dual boss engages a mating structure on the rear end of the needle hub, for unscrewing the needle from the handle.

Then the user pulls the vial, with its blood sample, rearward out of the handle. As the receptacle is withdrawn, the loosened needle comes with it, since the needle is still engaged with the stopper.

The needle moves rearward until the sharp forward point passes through the threaded hole in the transverse wall. With further rearward motion the needle is then trapped by its flange in the handle, allowing the collection vial and stopper to be separated from the needle. A separate rear cap is (or at least should be) applied over the rear skirt of the handle, to guard the sharp rear end of the needle.

In the Jagger hypodermic device, the needle is mounted by a relatively tight press fit to the forward end of a syringe that is fitted within the handle. The needle also extends in a relatively loose press fit through a hole in the front of the handle.

After use, the entire syringe must be pulled bodily out of the back end of the handle, carrying the needle rearward out of its front-end press fit with the handle, and into the cavity within the handle. The needle is carried in a flange that is too wide to escape from the rear end of the handle, and accordingly is pulled away from its tight press fit at the front end of the syringe.

The needle is thus trapped within the handle. The user must then dispose of the handle (with enclosed needle) and syringe separately.

The two forms of the Jagger invention — both the phlebotomy device and the hypodermic device — are undesirable in their arrangements for arming the apparatuses for retraction of the needle. By "arming" I refer to a process of discriminating between (1) operation of the device, for drawing blood or loading a syringe before injection; and (2) retraction of the needle, for disposal Phlebotomy-device operation includes moving each vacuum vial rearward and outward after it is full. Syringe operation includes filling the syringe, by pulling rearward and outward on the plunger, either in drawing blood or prior to an injection.

Thus, in Jagger's phlebotomy device and syringe alike, operation necessarily involves rearward motion of some kind. Retraction of course also involves rearward motion.

The apparatus must somehow be made so that it will not retract the needle during operation, but will retract the needle after operation. Jagger uses two different arming philosophies in her two different devices.

The two philosophies actually are opposite, and as a result have opposite drawbacks. Both sets of drawbacks, however, are severe.

I shall first consider the Jagger phlebotomy needle. Here an arming step is required, and the required step is unduly cumbersome.

As mentioned above, a user must unscrew the flange of the phlebotomy needle — using the last vacuum vial as a driver — before pulling the flange and needle back into the handle. This arrangement for retraction is likely to be bothersome to busy medical personnel, and therefore even more adverse to reliable, safe operation.

Now I shall turn to the Jagger hypodermic needle. In that device, proper syringe operation and proper retraction thereafter both depend upon maintenance of the design relationships between two friction-and-force relationships.

To fill the syringe a user must first advance the plunger fully forward, insert the needle tip into the liquid to be loaded, and then pull the plunger back. In pulling the plunger back, the user will most naturally grasp the outer handle or enclosure.

Thus the user relies upon relatively high friction between the needle-carrying nosepiece and the front end of the handle to keep the assembly together during loading. Later, however, the user relies upon relatively low friction between those same two parts to break the assembly down for needle retraction and disposal.

In essence, the device is supposed to be self-arming for retraction. The user does nothing to prepare for needle retraction after use, but rather depends upon two friction/force relationships to discriminate between loading and retraction.

These relationships, however, are too easily upset. For example, they can be disturbed by temperature variations, leakage of slippery or sticky substances, or improper insertion of the syringe tip into its mating receptacle at the rear of the needle flange.

In such circumstances the syringe can be extracted from the needle flange before the needle is retracted — leaving no proper means for retraction. Conversely, the syringe can be held too tightly in place in the handle, requiring separation by force — and so leading to accidental punctures, thereby defeating the purpose of the safety device.

All of this is a natural result of Jagger's syringe design, which attempts to avoid the necessity for a physical arming step on the part of the user. In effect Jagger's patent illustrates two opposing philosophies for retraction arming. One may be said to represent an excessive arming step, and the other an inadequate arming step. Both, however, tend toward the same result — a relatively ineffective device.

Other prior patents describe devices for automatic or semiautomatic resheathing of hypodermic syringes.

U.S. Pat. No. 4,026,287 to Haller is among the better of these, since it at least provides for retraction of the used needle into a cavity in a unitary, sturdy structure. The Haller device, however, requires screwing the syringe plunger into the back of the needle flange after use, to destroy a frangible seal around the flange and then retract the needle.

Haller, like Jagger, thus imposes an undue procedural burden on the user. Considered objectively, the amount of effort required to unthread the needle from the handle may be small; however, in this regard it is important to bear in mind a crucial psychological aspect of safety devices:

The additional procedure of unthreading the needle from its mount does not further any medical procedure which the user is assigned to perform, but only substitutes for placing a safety cap carefully over the needle. Consequently if personnel perceive the unthreading step required to make use of a particular safety feature as unduly burdensome, they simply will not use the safety features of the device at all.

If that happens regularly, then of course not only does the hazard persist but in addition the entire cost of the safety features is wasted. Seen in this light, the relatively small amount of effort involved in unthreading the needle is more correctly seen as a factor that controls the overall utility of the device.

Haller also fails to protect against inadvertent insertion of fingertips into the syringe barrel. U.S. Pat. No. 4,631,057 to Mitchell also leaves the needle accessible to fingertips through the unsealed forward end of the sheath.

Another patented device providing better frontal shielding against fingertip insertion in a vacuum-vial phlebotomy set is disclosed in U.S. Pat. No. 4,643,199 of Jennings, Jr. et al. That device has an auxiliary inner barrel, within the needle-holder handle, that is manipulated to retract the needle into the handle and lock it there.

The necessary manipulation involved is perhaps slightly less involved than in the Jagger device, but yet does include three separate motions: first a rotation (in a particular direction), then an axial telescoping motion, and finally another rotation (in the same particular direction). Furthermore an additional fourth separate motion is required to complete the task: locking a safety cap over the rear end of the auxiliary barrel.

Still other patented devices that provide good frontal shielding against fingertip insertion, but are otherwise remote from phlebotomy concerns, are U.S. Pat. Nos. 4,573,976 (Sampson) and 4,643,200 (Jennings, Jr.).

Worthy of mention for its provision of positive resistance to jarring of a syringe needle out of retracted position is U.S. Pat. No. 4,425,120 to Sampson et al. That device pays for its effective safety locking with complexity of the manual manipulations required in use. Similar observations apply to U.S. Pat. No. 3,890,971 to Leeson.

Numerous devices for providing merely visual shielding or screening of hypodermic syringes have been patented. Among these are U.S. Pat. Nos. 2,876,770 (White), 2,674,246 (Bower) and 3,134,380 (Armao). Such devices are actually counterproductive with respect to present purposes, since they effectively conceal the presence of a dangerously sharp and possibly contaminated needle.

Thus the prior art has failed to provide an optimum safety device for use under modern conditions in the field of the present invention. No prior-art device provides the necessary sure and easy operation that is essential to the effectiveness of such protection.

SUMMARY OF THE DISCLOSURE

My invention is a safety device for use in withdrawing liquid from a patient. It also serves thereafter to protect medical personnel, trash-handling personnel, and any other people who may have casual contact with the device after its use. The device protects all such individuals from contact with those portions of the device that have been within the patient.

My invention is intended for use with a separate liquid-receiving unit, which may be entirely conventional. In fact, if desired the liquid-receiving unit may be either of the two previously mentioned standard types that are commercially available for use with conventional phlebotomy sets.

As reflected in the appended claims, the liquid-receiving unit may be conceptualized either as a part of the combination of my invention or as a part of the context or environment in which the invention functions.

The device of my invention includes a hollow needle for piercing the patient, and for guiding and carrying a liquid out of the patient. The needle has a hollow shaft with at least one sharpened end, for receiving such liquid from the patient. The needle also has another end for discharging such liquid to the liquid-receiving unit.

My invention also has a needle holder, which in turn includes a handle suited to be grasped by a user of the device. The needle holder also must have some means for gripping the needle shaft and holding the needle in position.

For purposes of generality in description, I shall refer to these means as the "gripping means." By virtue of the gripping means, the previously mentioned "at least one sharpened end" of the needle projects forward for insertion into the patient — to receive the liquid from the patient.

The needle holder further includes a rearward-projecting skirt, which has two functions. First, the skirt generally shields the other end of the needle shaft (that is, the above-mentioned discharging end) against inadvertent contact with the user's hands. Second, the skirt permits access of the liquid-receiving unit to that "other end" of the needle shaft.

My invention further includes some manually actuable means for releasing the gripping means — and for retracting the sharp end of the needle. These means I shall, again for generality, call the "releasing and retracting means." Retraction of the needle by these means is substantially permanent, and substantially beyond reach of people's fingers.

In this regard it should be noted that some people have extremely small fingers, and that the needle may not be retracted beyond reach of extremely small fingers. For example, the fingers of very small children or infants might be inserted into an aperture through which a needle is retracted.

Children do not ordinarily have access to discarded medical equipment, and it is beyond the scope of my invention to attempt to guard against every conceivable remote hazard. Hence by the phrase "people's fingers" I mean to refer to fingers that are in a normal range of sizes for adult people.

The releasing and retracting means are manually actuable by a simple unitary rectilinear motion. By "simple unitary" motion I mean a motion that is not compound, one that entails a single-stage stroke or movement in just one direction.

Possibly the foregoing may be a summary of the preferred embodiments of my invention in their most general form. As will be appreciated, however, there are additional features which I prefer to incorporate in my invention to particularly optimize its efficacy. I shall mention some of those features here, reserving others for the detailed description that follows.

The releasing and retracting means preferably include a separate safety container for receiving and enclosing the entire needle for disposal. Through use of this type of releasing and retracting means, the needle is retracted and removed entirely from the handle. The handle itself thus may be made reusable with another needle.

The releasing and retracting means, particularly when in the form of a separate safety container, preferably include a fitting for manipulating the gripping means to release the needle. The fitting is at a forward end of the container, and accordingly can manipulate the gripping means when the container is pushed forward into the handle, in the simple unitary rectilinear motion mentioned above.

The releasing and retracting means also preferably include a rearward-biased retractor for engaging the needle and drawing it into the separate safety container. The invention when in this form also preferably includes a needle ferrule that is fixed along the exterior of the shaft, and configured to be gripped by the gripping means and engaged by the retractor.

The foregoing operational principles and advantages of the present invention will be more fully appreciated upon consideration of the following detailed description, with reference to the appended drawings, of which:

BRIEF DESCRIPTION OF THE DRAWINGS

FIG. 1 is a plan or side elevation of the needle and ferrule for a preferred embodiment of my invention.

FIG. 2 is a like view of the needle holder for the same embodiment.

FIG. 3 is an end-and-side perspective view of the same holder.

FIG. 4 is a greatly enlarged elevation, in longitudinal section, of the forward end of the same holder, showing the needle and ferrule held in position by the gripping means.

DETAILED DESCRIPTION OF THE PREFERRED EMBODIMENTS

Figure 5:
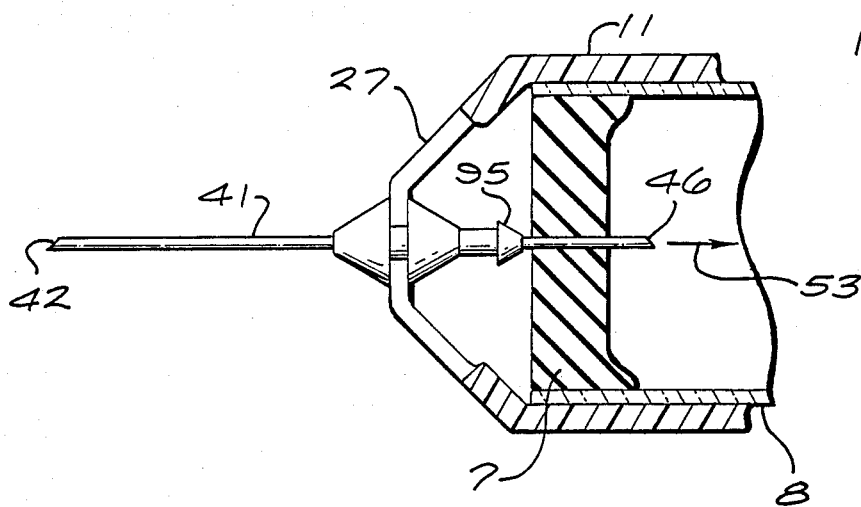
FIG. 5 is a similar view, but slightly smaller, showing a collection vial in place within the needle holder for receiving liquid from a patient.

As shown in FIGS. 1 through 12, an embodiment of my invention which I now prefer includes a needle 9. The needle has a hollow shank 41. The shank has a sharpened forward end or tip 42 for piercing a patient to withdraw blood or other liquid, and another end 96 for receiving liquid through the shank and transmitting it to a collection device.

The other end 96 preferably is also sharpened, for piercing an elastomeric stopper in a vacuum vial; however, my invention is alternatively usable with a remote collection receptacle and an interconnecting tube. When designed for use in that way, the rearward end 96 of the needle is preferably not sharpened and in fact is preferably made blunt and smooth for ease of tube attachment.

Fixed securely to the shank 41, usually somewhat rearward of its midpoint, is a shaped ferrule 40. The ferrule has a forwardmost section 43 and a central abutment section 44 that is used in initiating the retraction procedure.

The ferrule also has an engagement section 95 that is used in the retraction step itself. Formed in the ferrule 40 between the forward section 43 and the abutment section 44 is a circumferential groove 91 which is gripped by the gripping means of the needle holder.

Completing the needle assembly 40 when new are a pair of safety caps or sheaths 101, 102 — one over each end of the shank 41. The safety caps may be fastened by forming directly to the ferrule, if desired, and thus used as an indication that the needle is new.

The needle 9 with its ferrule 40 and safety caps 101, 102 is preferably supplied for use separately from the needle holder, since the latter is reusable. The caps are designed to be readily snapped off and discarded before the needle is used; they will not be reused.

If the rear end 96 of the needle is sharp, as illustrated, a user may prefer to keep the rear safety cap in place until the needle is mounted in the holder. If that rear end 96 of the needle is blunt, however, the rear safety cap 102 may be omitted entirely.

The needle holder 10 (FIGS. 2 through 5) has a generally cylindrical handle 11, advantageously knurled or otherwise finished to provide a comfortable and secure surface to be grasped by a user. The rearward end 12 of the cylindrical handle 11 is open; it is this rearward cylindrical portion with its open end 12 that is referred to herein as the "skirt."

The forward end of the needle holder 10 has a transverse end wall 15, 27. The radially central portions of this wall terminate in inward-extending thin leaves 27, which fit into the ferrule groove 91 as shown in FIG. 4 to secure the needle axially.

At the center of the leaves 27 is an orifice for receiving the ferrule groove 91. The radially outer portion 15 of the end wall may also be angled forward toward the leaves 27.

To install the needle 9 in the holder 10, a user removes the rear safety cap 102, and inserts the needle by rearward motion into the aperture 97. The engagement segment 44 of the ferrule 40 is tapered to spread the leaves 27 apart as the needle is inserted.

When the groove 91 reaches the leaves 27, the leaves snap inward into the groove and firmly hold the ferrule 40 and needle 9 in position. The user then removes the front safety cap 101. The assembly is now ready for use.

Even apart from infection-hazard considerations, this procedure is a considerable improvement over that required with prior phlebotomy sets. In the conventional assembly procedure, as mentioned above, the user must thread the needle into the handle.

By comparison the simple, unitary assembly motion used with my invention saves time and effort, and avoids the risk of crossthreading the parts. It also reduces risk of painful puncture.

Withdrawing blood or other body fluid by use of the invention is generally conventional. First the sharp end 42 of the needle shank 41 is inserted into the patient's body and positioned as desired.

Next a conventional or other vacuum vial 8 (FIG. 5) is inserted from the rear through the skirt 12 until the stopper or wall 7 at the forward end of the vial is impaled on the sharp rear end 96 of the needle. Blood or other liquid then flows along a path 53 into the vacuum vial from the rear end 96 of the hollow shank 41.

Flow is driven by the difference between the patient's blood pressure (or other pressure at the site within the patient's body from which liquid is being removed) and the lowered pressure inside the vial. This flow continues until the vial is full or the user withdraws the vial from the needle.

If desired, two or more vials can be filled or partially filled in this way — all as well known to medical staff members familiar with present-day devices. The practice of my invention thus requires no new education or training as to the drawing of blood or other liquid.

After the final vial has been filled or partially filled, the user will generally withdraw the needle from the patient's body in the conventional fashion. The user will then initiate retraction, i.e., after the needle has been removed from the patient.

In principle, if desired, retraction of the needle may be initiated while the tip is still in the patient's body. Particularly if the patient is conscious, however, the motions and forces involved in initiating retraction are likely to cause at least some slight discomfort to the patient. In any event there is ordinarily no reason to keep the needle tip in the patient's body after liquid withdrawal is complete, and it will be preferred to remove the needle from the patient's body before proceeding.

Figure 6:
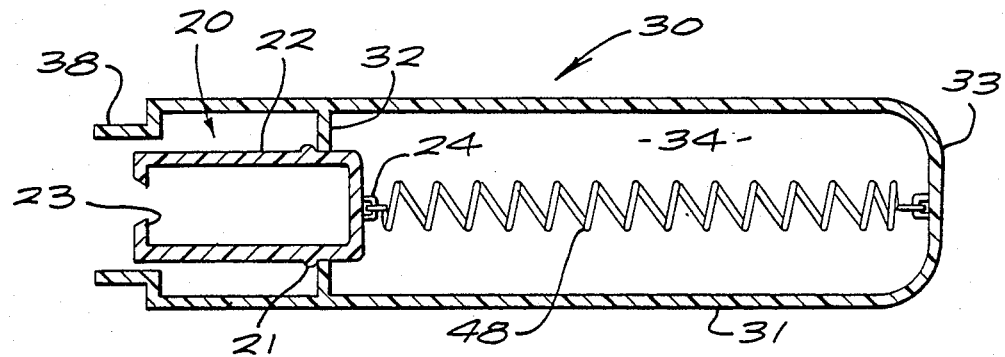
FIG. 6 is a longitudinal section of the separate safety container, with the retractor and biasing device included.
Figure 7:
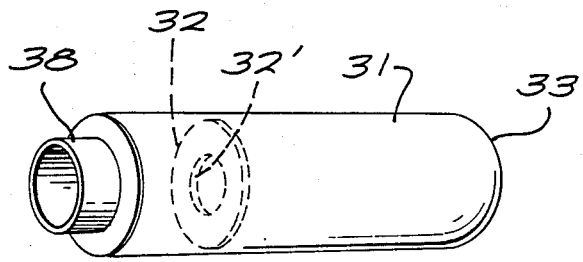
FIG. 7 is an end-and-side perspective view of the same container without the retractor and biasing device.
Figure 8:
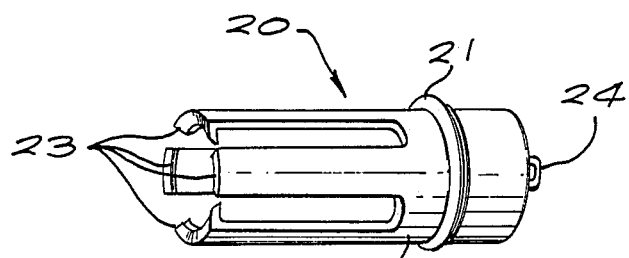
FIG. 8 is a greatly enlarged perspective view of the retractor alone.

As shown in FIGS. 6 through 8, the preferred embodiment of my invention also includes releasing and retracting means in the form of a separate safety container 30 with a retractor 20. The safety container 30 has a generally elongated barrel 31, small enough in diameter to fit into the hollow handle 11 of the needle holder 10.

To minimize the likelihood of inadvertent premature retraction of the needle, I prefer to manufacture the barrel 31 to appear and feel distinctly different from the vacuum vials 8 (FIG. 5). Thus it should be brightly colored, preferably with a conspicuous striped or other distinctive pattern (not shown), and should have a coarsely grooved or otherwise coarsely textured outside surface.

In addition it should conspicuously carry the standard biohazard-warning symbol. The shape of the rearward end 33 is advantageously made distinctly different from that of the vacuum vials.

Within the barrel, spaced back from its open forward mouth, is an internal flange 32. Positioned within this flange 32 is a retractor 20, which is spring-loaded rearward but prevented by a circumferential boss or detent 21 from passing entirely through the central hole of the internal flange 32.

The retractor 20 also carries a spring anchor 24. Within the rear chamber 34 of the container 30 is a tension spring 48, anchored at its forward end to the retractor anchor 24 and at its rearward end to the rear wall 33 of the container 30. The spring biases the retractor toward the rear chamber 34 and rear wall 33, but is not strong enough to pull the retractor boss or detent 21 past the internal flange 32.

The forward end of the retractor is formed as four hooks 23, which are shaped to receive and grapple the engagement structure 95 at the rear of the needle ferrule 40. The hooks are sized to push against the abutment segment 44 at the center of the ferrule 40 after the hooks are engaged with the engagement structure 95.

By means of that abutment and pushing action, the abutment segment is able to push the retractor 20 rearward so that its boss or detent 21 passes the internal flange 32 and thereby enters the rear chamber 34 of the safety container 30. Once the boss 21 is past the flange 32, the spring 48 biases the retractor 20, hooks 23 and attached engagement structure 95 into the rear chamber — restrained only by the grip between the leaves 27 and the ferrule groove 91.

The forward end of the barrel 31 carries a forward-projecting fitting 38, of length and diameter sized to engage the interior sloping surfaces of the leaves 27 (FIG. 4), to spread the leaves and permit retraction of the needle. The fitting 38 is sized to fully engage the leaves after the hooks 23 have pushed the retractor boss or detent 21 through the internal flange 32 as previously described.

Figure 9:
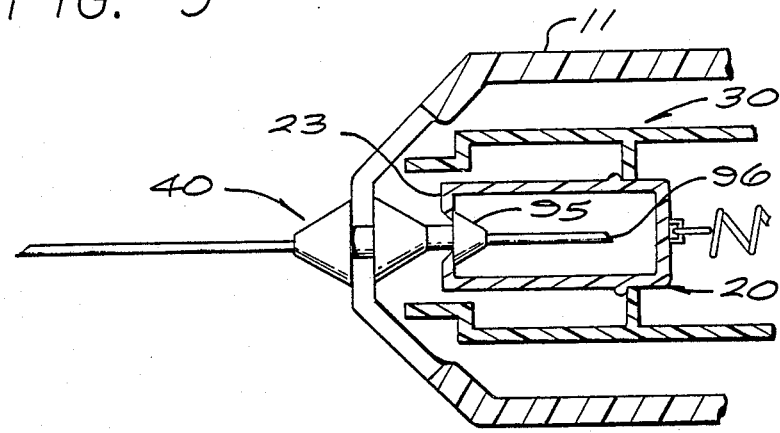
FIGS. 9 through 11 are a series of views of the front end of the separate safety container, in longitudinal section, showing the safety container in use — that is, in the process of releasing and retracting the needle and ferrule from the needle holder.

It should now be clear that the releasing and retracting means operate as shown in FIGS. 9 through 12. When the safety container 30 is inserted into the needle holder 11, first the hooks 23 pass the engagement structure 95 — so that the retractor 20 is secured by the engagement structure 95 to the ferrule 40 as shown in FIG. 9.

Figure 10:
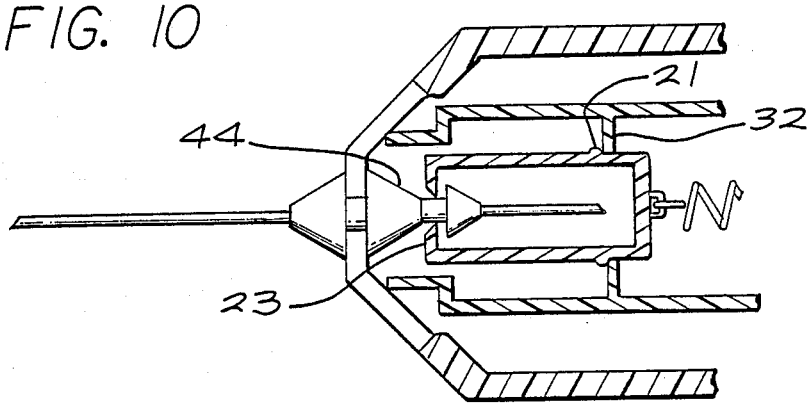

As the container 30 is advanced further into the holder 11, next the abutment segment 44 pushes the hooks 23 rearward so that the circumferential boss 21 passes the internal flange 32. This condition is shown in FIG. 10.

This step is accomplished by slight distortions of both the retractor shell 22 and the flange 32. The spring 48 then pulls the retractor 20 back until the hooks 23 firmly engage the engagement structure 95.

Figure 11:
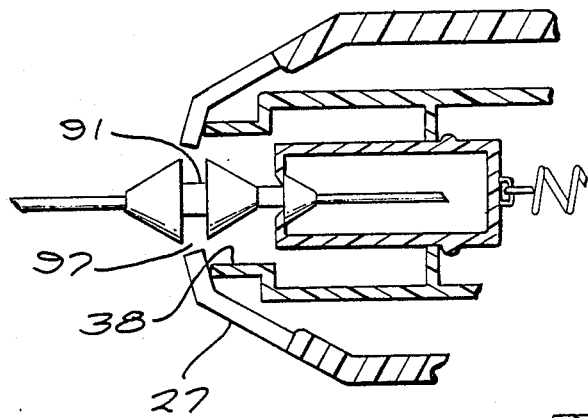
Figure 12:
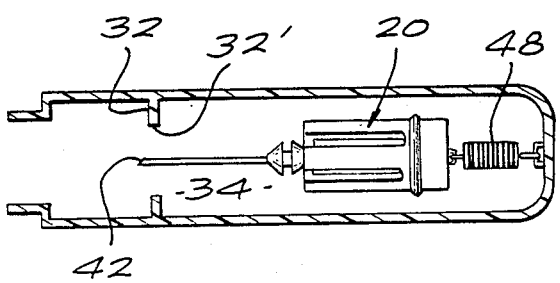
FIG. 12 is a side view of the entire safety container with the retracted needle and ferrule safely received inside.

As the container 30 is advanced still further, its forward fitting 38 engages and forces apart the leaves 27, as shown in FIG. 11. This action releases the entire ferrule and needle for retraction past the flange 32, through its central aperture 32', and into the rear chamber toward the rest position illustrated in FIG. 12.

Substantially the same system can be used with a collection system that employs a remote receptacle and tubing. With such a system, as mentioned earlier, the needle may have a blunt rearward end. In other respects, however, the retraction mechanism and procedure can be just as described above.

My invention is particularly advantageous in that the safety container consists of only three parts, all inexpensively made: the barrel with its integral fitting and flange, the retractor, and the spring. The needle holder, also inexpensively manufactured, is reusable for a great many needles. The needle itself is no more costly than a conventional needle.

Use of my invention is much easier and faster than prior devices that require threading or multiple-motion latching of the needle assembly, and requires no additional procedure of affixing a safety cap to complete the securing of the needle ends.

Furthermore my invention does not subject the stopper of a full vacuum vial to possible damage. My invention avoids this possible problem in that it does not use a vial as a tool for releasing the needle while the needle is still penetrating the stopper.

It will be understood that the foregoing disclosure is intended to be merely exemplary, and not to limit the scope of the invention — which is to be determined by reference to the appended claims.

I claim:

1. A safety device for use in withdrawing liquid from a patient and for thereafter protecting people from contact with portions of the device that have been within the patient; said device being for use with a liquid-receiving unit; and said device comprising:
   a hollow needle for piercing such patient and for guiding and carrying such liquid into or out of the patient, said needle having a hollow shaft with at least one sharpened end, for receiving such liquid from the patient, and another end for discharging such liquid to such liquid-receiving unit;
   a needle holder that includes:
      a handle suited to be grasped by a user of the device,
      means, secured to the handle, for gripping the needle shaft and holding the needle in position with its sharpened and projecting forward from the handle for insertion into such patient to receive such liquid through the hollow shaft from such patient, and
      a skirt, projecting rearward from the handle, for generally shielding the other end of the needle shaft against inadvertent contact with the user's hands, while permitting access of such liquid-receiving unit to said other end of the needle shaft;
   manually actuable means for releasing the gripping means and for substantially permanently retracting the sharp end of the needle beyond reach of such people's fingers;
   wherein the releasing and retracting means are manually actuable, and comprise a separate safety container for receiving and enclosing the entire needle for disposal;
   whereby the needle is retracted and removed entirely from the handle.

2. The safety device of claim 1, wherein: the handle is reusable with another needle.

3. The safety device of claim 5, wherein:
   the gripping means comprise radially inward extending leaves at a forward end of the handle, for securing the needle axially; and
   the fitting comprises a forward-extending structure for spreading the leaves.

4. The safety device of claim 3, wherein:
   the leaves extend from the handle radially inward and axially forward at an angle to the needle shaft; and
   the forward-extending structure of the releasing and retracting means, when moved forward within the handle against the leaves, spreads the leaves radially outward and axially forward.

5. The safety device of claim 1, wherein:
   the releasing and retracting means comprise a fitting, at a forward end of the container, for manipulating the gripping means to release the needle when the container is pushed forward into the handle in said simple unitary rectilinear motion.

6. The safety device of claim 5, in further combination with:

said liquid-receiving unit, in the form of a vial that is sealed at a forward end by a piercable wall, and that is supplied at a reduced internal pressure for use.

7. The safety device of claim 5, in further combination with:

said liquid-receiving unit, in the form of a standard phlebotomy vial, adapted for use with standard phlebotomy sets that do not retract needles;

said standard phlebotomy vial being sealed at a forward end by a piercable wall, and supplied at a reduced internal pressure for use.

8. The safety device of claim 5, in further combination with:

said liquid-receiving unit in the form of a remote receptacle, at a reduced internal pressure, communicating with the safety device through a liquid-conveying tube.

9. The safety device of claim 5, in further combination with:

said liquid-receiving unit in the form of a standard phlebotomy collection unit, adapted for use with standard phlebotomy sets that do not retract needles;

said standard phlebotomy collection unit comprising a remote receptacle, at a reduced internal pressure, communicating with the safety device through a liquid-conveying tube.

10. The safety device of claim 1, wherein:

the releasing and retracting means comprises a rearward-biased retractor for engaging the needle and drawing it into the separate safety container.

11. The safety device of claim 10, further comprising:

a needle ferrule fixed along the exterior of the shaft and configured to be gripped by the gripping means and to be engaged by the retractor.

12. The safety device of claim 10, wherein:

the releasing and retracting means further comprise a detent for deterring premature rearward motion of the retractor into the safety container; and the retractor is sized to butt against the ferrule to force the retractor rearward past the detent after the retractor has engaged the ferrule.

13. The safety device of claim 10, further comprising:

a needle ferrule fixed along the exterior of the shaft and having a circumferential groove;

wherein the gripping means comprise a plurality of leaves, at a forward end of the handle, that extend from the handle radially inward and axially forward at an angle to the needle shaft for insertion into the circumferential groove to secure the needle axially; and the fitting comprises a forward-extending structure which, when moved forward within the handle against the leaves, spreads the leaves radially outward and axially forward to release the needle axially for retraction.

14. The safety device of claim 13, wherein:

the releasing and retracting means further comprise a detent for deterring premature rearward motion of the retractor into the safety container; and the retractor is sized to butt against the ferrule to force the retractor rearward past the detent after the retractor has engaged the ferrule.

15. The safety device of the claim 14, wherein:

the separate safety container has a forwardly open mouth of transverse dimension large enough to pass the needle and ferrule but too small to pass such people s fingers; and the detent forms a radially inward-projecting flange along an interior wall of the separate safety container, recessed axially inward from the container mouth by a distance that is greater than the transverse dimension of the container mouth;

the flange defines an aperture that is large enough to pass the needle and ferrule but too small to pass such people's fingers;

whereby the needle when retracted into the separate safety container is doubly guarded from such people's fingers.

16. The safety device of claim 14, in further combination with:

said liquid-receiving unit, in the form of a vial that is sealed at a forward end by a piercable wall, and that is supplied at a reduced internal pressure for use.

17. The safety device of claim 14, in further combination with:

said liquid-receiving unit, in the form of a standard phlebotomy vial, adapted for use with standard phlebotomy sets that do not retract needles;

said standard phlebotomy vial being sealed at a forward end by a piercable wall, and supplied at a reduced internal pressure for use.

18. The safety device of claim 14, in further combination with:

said liquid-receiving unit in the form of a remote receptacle, at a reduced internal pressure, communicating with the safety device through a liquid-conveying tube.

19. The safety device of claim 14, in further combination with:

said liquid-receiving unit in the form of a standard phlebotomy collection unit, adapted for use with standard phlebotomy sets that do not retract needles;

said standard phlebotomy collection unit comprising a remote receptacle, at a reduced internal pressure, communicating with the safety device through a liquid-conveying tube.

20. The safety device of claim 1, wherein:

the separate safety container has a forwardly open mouth that is large enough to pass the needle but too small to pass such people's fingers.

21. The safety device of claim 1, in further combination with:

said liquid-receiving unit, in the form of a vial that is sealed at a forward end by a piercable wall, and that is supplied at a reduced internal pressure for use.

22. The safety device of claim 1, in further combination with:

said liquid-receiving unit, in the form of a standard phlebotomy vial, adapted for use with standard phlebotomy sets that do not retract needles;

said standard phlebotomy vial being sealed at a forward end by a piercable wall, and supplied at a reduced internal pressure for use.

23. The safety device of claim 1, in further combination with:

said liquid-receiving unit in the form of a remote receptacle, at a reduced internal pressure, communicating with the safety device through a liquid-conveying tube.

24. The safety device of claim 1, in further combination with:
- said liquid-receiving unit in the form of a standard phlebotomy collection unit, adapted for use with standard phlebotomy sets that do not retract needles;
- said standard phlebotomy collection unit comprising a remote receptacle, at a reduced internal pressure, communicating with the safety device through a liquid-conveying tube.

25. The device of claim 1, wherein:
- the releasing and retracting means comprise means for preventing escape of the sharp end of the needle after actuation of the releasing and retracting means.

26. A device for use in withdrawing liquid from a patient and for thereafter protecting people from contact with portions of the device that have been within the patient; said device being for use with a liquid-receiving unit; and said device comprising:
- a hollow needle for piercing such patient and for guiding and carrying such liquid into or out of the patient, said needle having a hollow shaft with at least one sharpened end, for receiving such liquid from the patient, and another end for discharging such liquid to such liquid-receiving unit;
- a needle holder that includes:
    - a handle suited to be grasped by a user of the device,
    - means, secured to the handle, for gripping the needle shaft and holding the needle in position with its sharpened end projecting forward from the handle for insertion into such patient to receive such liquid through the hollow shaft from such patient, and
    - a skirt, projecting rearward from the handle, for generally shielding the other end of the needle shaft against inadvertent contact with the user's hands, while permitting access of such liquid-receiving unit to said other end of the needle shaft;
- manually actuable means for releasing the gripping means and for substantially permanently retracting the sharp end of the needle beyond reach of such people's fingers;
- wherein the releasing and retracting means are manually actuable, and comprise:
    - means for preventing escape of the sharp end of the needle after actuation of the releasing and retracting means, and
    - a spring disposed and attached to propel the sharp end of the needle into the releasing and retracting means, when the releasing and retracting means are manually actuated.

27. The device of claim 26, wherein:
- the releasing and retracting means comprise a separate safety container for receiving and enclosing the entire needle for disposal;
- whereby the needle is retracted and removed entirely from the handle.

* * * * *